(12) United States Patent
Cheeran et al.

(10) Patent No.: US 12,011,585 B2
(45) Date of Patent: Jun. 18, 2024

(54) METHODS FOR PROGRAMMING A DEEP BRAIN STIMULATION SYSTEM AND A CLINICIAN PROGRAMMER DEVICE

(71) Applicant: Advanced Neuromodulation Systems, Inc., Plano, TX (US)

(72) Inventors: Binith J Cheeran, Austin, TX (US); Jonathan P. Avedikian, Plano, TX (US); Brittany L. Boudreau, Grapevine, TX (US); Jason Pounds, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 18/127,448

(22) Filed: Mar. 28, 2023

(65) Prior Publication Data

US 2023/0233846 A1 Jul. 27, 2023

Related U.S. Application Data

(60) Continuation of application No. 17/315,660, filed on May 10, 2021, now Pat. No. 11,642,517, which is a division of application No. 16/164,675, filed on Oct. 18, 2018, now Pat. No. 11,033,732.

(60) Provisional application No. 62/579,617, filed on Oct. 31, 2017.

(51) Int. Cl.
| | |
|---|---|
| *A61N 1/05* | (2006.01) |
| *A61N 1/36* | (2006.01) |
| *A61N 1/372* | (2006.01) |
| *A61N 1/378* | (2006.01) |
| *G06F 3/0482* | (2013.01) |

(Continued)

(52) U.S. Cl.
CPC ....... *A61N 1/0534* (2013.01); *A61N 1/36132* (2013.01); *A61N 1/36135* (2013.01); *A61N 1/36146* (2013.01); *A61N 1/36157* (2013.01); *A61N 1/36164* (2013.01); *A61N 1/37241* (2013.01); *A61N 1/37247* (2013.01); *A61N 1/378* (2013.01); *G06F 3/0482* (2013.01); *G16H 10/60* (2018.01); *G16H 40/40* (2018.01); *A61N 1/36192* (2013.01); *A61N 1/37252* (2013.01)

(58) Field of Classification Search
CPC .............. A61N 1/0534; A61N 1/36132; A61N 1/37247; A61N 1/378; A61N 1/36135; A61N 1/36146; A61N 1/36157; A61N 1/37241; A61N 1/36192; G06F 3/0482; G16H 40/40
See application file for complete search history.

(56) References Cited

U.S. PATENT DOCUMENTS

| | | |
|---|---|---|
| 2008/0027514 A1 | 1/2008 | DeMulling et al. |
| 2010/0010392 A1 | 1/2010 | Skelton et al. |

*Primary Examiner* — Paula J Stice
(74) *Attorney, Agent, or Firm* — Norton Rose Fulbright US LLP

(57) ABSTRACT

In some embodiments, a clinician programmer device for controlling a deep brain stimulation (DBS) system is adapted to assist a clinician to conduct an electrode screening review for the DBS system including screening of segmented electrodes. The clinician programmer stores software code for conducting a screening review in memory. The software code may comprise: code for providing one or more interface screens for guiding the user of the device through testing of electrode configurations of the implantable stimulation lead, wherein the code for providing applies at least one testing progression for guiding the user of the device through a defined testing order.

20 Claims, 15 Drawing Sheets

(51) Int. Cl.
*G16H 10/60* (2018.01)
*G16H 40/40* (2018.01)

| Cancel | Benefit | Add |
|---|---|---|

| Electrode 1 | 0.50 mA |
|---|---|

| Partial | ✓ |
|---|---|
| Complete | |

| Action Tremor | ✓ |
|---|---|
| Bradykinesia | |
| Dyskinesia | |
| Dystonia | |
| Gait | |
| Rest Tremor | |
| Rigidity | ✓ |
| Speech | |

Edit Benefit List

NOTES

| Cancel | Side Effect | Add |
|---|---|---|

| Electrode 1 | 3.00 mA |
|---|---|

| Transient | |
|---|---|
| Sustained | ✓ |

| Ataxia | |
|---|---|
| Dizziness | |
| Dyskinesia | |
| Hypomania | |
| Muscle Contraction | ✓ |
| Mile | Moderate | Severe |
| Nausea | |
| Oculomotor | |
| Other Cognitive/Behavioral Effect | |
| Pain | |
| Paresthesia | |
| Parkinsonism | |
| Postural Disturbance | |
| Tremor | |
| Speech Disturbance | |

Edit Side Effect List

METHODS FOR PROGRAMMING A DEEP BRAIN STIMULATION SYSTEM AND A CLINICIAN PROGRAMMER DEVICE

CROSS-REFERENCE TO RELATED APPLICATIONS

The present application is a continuation of U.S. patent application Ser. No. 17/315,660 filed May 10, 2021, which is a division of U.S. patent application Ser. No. 16/164,675 filed Oct. 18, 2018, which claims the benefit of U.S. Provisional Application No. 62/579,617 filed Oct. 31, 2017, the disclosures of which are incorporated by reference herein in their entirety.

TECHNICAL FIELD

This application is generally related to methods for programming a deep brain stimulation system and a clinician programmer device.

BACKGROUND INFORMATION

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

A deep brain stimulation procedure typically involves first obtaining preoperative images of the patient's brain (e.g., using computer tomography (CT) or magnetic resonance imaging (MRI)). Using the preoperative images, the neurosurgeon can select a target region within the brain, an entry point on the patient's skull, and a desired trajectory between the entry point and the target region. In the operating room, the patient is immobilized and the patient's actual physical position is registered with a computer-controlled navigation system. The physician marks the entry point on the patient's skull and drills a burr hole at that location. Stereotactic instrumentation and trajectory guide devices are employed to control the trajectory and positioning of a lead during the surgical procedure in coordination with the navigation system.

Brain anatomy typically requires precise targeting of tissue for stimulation by deep brain stimulation systems. For example, deep brain stimulation for Parkinson's disease commonly targets tissue within or close to the subthalamic nucleus (STN). The STN is a relatively small structure with diverse functions. Stimulation of undesired portions of the STN or immediately surrounding tissue can result in undesired side effects. For example, muscle contraction or muscle tightening may be caused by stimulation of neural tissue that is near the STN. Mood and behavior dysregulation and other psychiatric effects have been reported from undesired stimulation of neural tissue near the STN in Parkinson's patients.

To avoid undesired side effects in deep brain stimulation, neurologists often attempt to identify a particular electrode for stimulation that only stimulates the neural tissue associated with the symptoms of the underlying disorder while avoiding use of electrodes that stimulate other tissue. Also, neurologists may attempt to control the pulse amplitude, pulse width, and pulse frequency to limit the stimulation field to the desired tissue while avoiding other tissue.

As an improvement over conventional deep brain stimulation leads, leads with segmented electrodes have been proposed. Conventional deep brain stimulation leads include electrodes that fully circumscribe the lead body. Leads with segmented electrodes include electrodes on the lead body that only span a limited angular range of the lead body. The term "segmented electrode" is distinguishable from the term "ring electrode." As used herein, the term "segmented electrode" refers to an electrode of a group of electrodes that are positioned at approximately the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120 degrees about the outer diameter of the lead body. By selecting between such electrodes, the electrical field generated by stimulation pulses can be more precisely controlled and, hence, stimulation of undesired tissue can be more easily avoided.

An example of a deep brain stimulation lead is the INFINITY™ directional lead manufactured by Abbott (Plano, TX). The INFINITY™ directional lead includes two conventional electrodes and two sets of segmented electrodes. The two sets of segmented electrodes are positioned in between the two conventional electrodes. Each set of segmented electrodes includes three segmented electrodes distributed about the circumference of the lead at a given axial position. The INFINITY™ deep brain stimulation system includes a clinician programmer that permits the neurologist or other clinician to program the DBS implantable pulse generator to deliver electrical pulses through the various electrodes of the INFINITY™ directional leads.

Although DBS stimulation leads with segmented electrodes provide an opportunity to tailor the stimulation therapy in a manner that is not possible with conventional leads, programming DBS systems that include segmented electrodes may be challenging for neurologists and other health care professionals. Specifically, clinicians responsible for programming DBS systems are allocated a limited amount of time to select DBS program parameters for a patient's DBS therapy. The increased number of active electrode possibilities in combination with other DBS parameters increases the complexity of determining an optimal DBS therapy for a given patient.

SUMMARY

In some embodiments, a clinician programmer device is adapted or configured to control a deep brain stimulation (DBS) system. The clinician programmer comprises: a display; user input circuitry for receiving input from a user of the device; memory for storing executable instructions and data; a processor for controlling operations of the clinician programmer according to executable instructions; and wireless communication circuitry for conducting wireless communications with an implantable pulse generator after implantation within a patient. The memory of the clinician programmer stores software code for conducting a screening review of electrodes of an implantable stimulation lead coupled to the implantable pulse generator, wherein the electrodes of the implantable stimulation lead include at least one set of segmented electrodes.

In some embodiments, the software code comprises: (a) code for providing one or more interface screens for guiding the user of the device through testing of electrode configurations of the implantable stimulation lead, wherein the code for providing applies at least one testing progression for guiding the user of the device through a defined testing order, wherein the at least one testing progression includes (i) testing all segmented electrodes of a common level as active DBS electrodes and (ii) testing each segmented electrode of the common level as a single active DBS electrode; (b) code for controlling delivery of deep brain stimulation to the patient by communication with the implantable pulse generator for each tested electrode configuration, wherein the code for controlling modifies a DBS pulse amplitude for each tested electrode configuration; and (c) code for receiving identification of a therapeutic window for one or more DBS parameters for each tested electrode configuration, wherein the therapeutic window is defined by one or more DBS parameters used for test stimulation for a DBS benefit and a DBS side effect experienced by the patient during testing. In some embodiments, the code for receiving identification records a side effect amplitude value in response receiving input from the user of the device to indicate that the user has experienced a side effect and the code for controlling automatically decreases the DBS pulse amplitude to an amplitude value below the recorded amplitude value. In some embodiments, the code for controlling automatically decreases the DBS pulse amplitude without substantially interrupting deep brain stimulation of the patient according to an electrode configuration under test.

In some embodiments, the software code further comprises: code for comparing therapeutic windows for each tested electrode configuration to a target value and code for alerting a user of the device that the target value has been reached. In some embodiments, the code for alerting receives input from the user of the device whether to skip additional electrode screening after the target value has been reached. In some embodiments, the software code further comprising: code for comparing power requirements associated with the therapy thresholds for the tested electrode configuration to inform the user of the device whether each electrode configuration is likely to provide an optimal DBS program for the patient. In some embodiments, the software code further comprises: code for suggesting omission of testing of one or more electrode configurations based on screening review data previously recorded for the patient by the code of receiving identification.

In some embodiments, the software code comprises: (a) code for providing one or more interface screens for guiding the user of the device through testing of electrode configurations of the implantable stimulation lead, wherein the code for providing applies different progressions for electrode testing depending upon an identification of an electrode or electrode level to begin a screening review session; (b) code for controlling delivery of deep brain stimulation to the patient by communication with the implantable pulse generator for each tested electrode configuration, wherein the code for controlling modifies a DBS pulse amplitude for each tested electrode configuration; and (c) code for receiving identification of a therapeutic window for one or more DBS parameters for each tested electrode configuration, wherein the therapeutic window is defined by one or more DBS parameters used for test stimulation for a DBS benefit and a DBS side effect experienced by the patient during testing.

In some embodiments, the code for providing evaluates therapeutic window parameters for a first set of segmented electrodes and a second set of electrodes. In some embodiments, the code for providing omits screening of one ring electrode depending upon a comparison of the therapeutic window parameters for the first and second sets of segmented electrodes. In some embodiments, the code for providing changes an order of testing individual segmented electrodes depending upon a comparison of the therapeutic window parameters for the first and second sets of segmented electrodes.

In some embodiments, the software code comprises: (a) code for providing one or more interface screens for guiding the user of the device through testing of electrode configurations of the implantable stimulation lead, wherein the code for providing applies at least a first progression and a second progression for electrode testing in series, and wherein the second progression is selected from at least two options according to patient response data obtained during the first progression; (b) code for controlling delivery of deep brain stimulation to the patient by communication with the implantable pulse generator for each tested electrode configuration, wherein the code for controlling modifies a DBS pulse amplitude for each tested electrode configuration; and (c) code for receiving identification of a therapeutic window for one or more DBS parameters for each tested electrode configuration, wherein the therapeutic window is defined by one or more DBS parameters used for test stimulation for a DBS benefit and a DBS side effect experienced by the patient during testing.

In some embodiments, the code for providing evaluates therapeutic window parameters for a first set of segmented electrodes and a second set of electrodes. In some embodiments, the code for providing selects an option from the at least two options by comparing the therapeutic window parameters for a first set of segmented electrodes and a second set of electrodes. The at least two options may define different sets of segmented electrodes for screening.

In some embodiments, the software code comprises: (a) code for providing one or more interface screens for guiding the user of the device through testing of electrode configurations of the implantable stimulation lead; (b) code for controlling delivery of deep brain stimulation to the patient by communication with the implantable pulse generator for each tested electrode configuration, wherein the code for controlling modifies a DBS pulse amplitude for each tested electrode configuration; and (c) code for receiving identification of a therapeutic window for one or more DBS parameters for each tested electrode configuration, wherein the therapeutic window is defined by one or more DBS parameters used for test stimulation for a DBS benefit and a DBS side effect experienced by the patient during testing, wherein the code for controlling automatically reduces a DBS pulse amplitude in response to the user of the device providing input to the code for receiving to identify a side effect experienced by the patient.

In some embodiments, the code for providing evaluates therapeutic window parameters for a first set of segmented electrodes and a second set of electrodes. In some embodiments, the code for providing omits screening of one ring electrode depending upon a comparison of the therapeutic window parameters for the first and second sets of segmented electrodes. In some embodiments, the code for providing changes an order of testing individual segmented electrodes depending upon a comparison of the therapeutic window parameters for the first and second sets of segmented electrodes.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 4 depicts a GUI dialog for entry of patient response data according to some embodiments.

FIG. 5 depicts a GUI dialog for entry of patient response data according to some embodiments.

DETAILED DESCRIPTION

The present application is generally related to systems and methods for providing deep brain stimulation (DBS) therapy to a patient using a DBS system that includes one or more directional leads. In some embodiments, a clinician programmer device includes clinician software that permits a neurologist or other health care clinician to evaluate a patient's response to deep brain stimulation applied through various conventional ring and segmented electrodes of directional lead. The clinician programmer guides the health care professional through electrodes and electrode combinations in an efficient manner while permitting the clinician to monitor beneficial therapeutic results and avoiding adverse or unwanted side effects. The review of the patient response using the various electrodes and electrode combinations enables the clinician to arrive at an optimal DBS program to treat the patient's neurological disorder.

Figure 1:
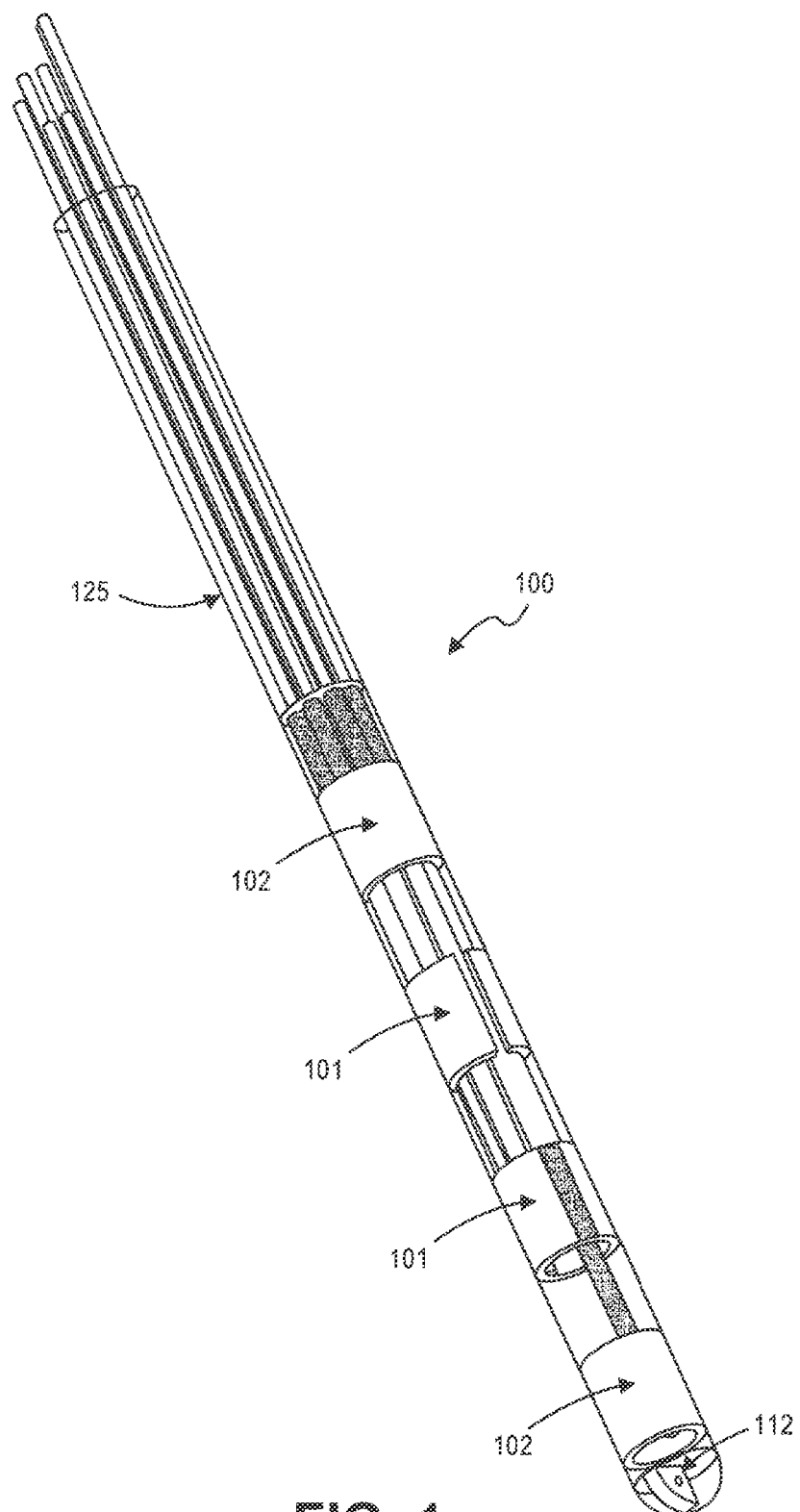
FIG. 1 depicts a tip of a deep brain stimulation lead that may be employed according to some embodiments.

FIG. 1 depicts a distal portion of deep brain stimulation lead 100 that may be used according to some embodiments. DBS lead 100 includes two sets of segmented electrodes 101 that are located in between two conventional electrodes 102 (referred to as a 1-3-3-1 configuration). Stimulation lead 100 may include a radio-opaque feature or other imaging feature 112 that permits the orientation of lead 100 to be determined after it is implanted at a suitable DBS location. The various electrodes are connected to hypotubes 125 which are embedded in molded polymer material. The fabrication of DBS lead 100 may occur using suitable implantable device fabrication processes such as the processes described in U.S. Patent App. Pub. No. 20160263370, entitled "MEDICAL LEADS WITH SEGMENTED ELECTRODES AND METHODS OF FABRICATION THEREOF," which is incorporated herein by reference. The INFINITY™ directional lead manufactured by Abbott (Plano, TX) may be used according to some embodiments. Although one specific configuration is shown in FIG. 1, any suitable configuration of electrodes and any suitable directional lead may be employed according to some embodiments.

Figure 2:
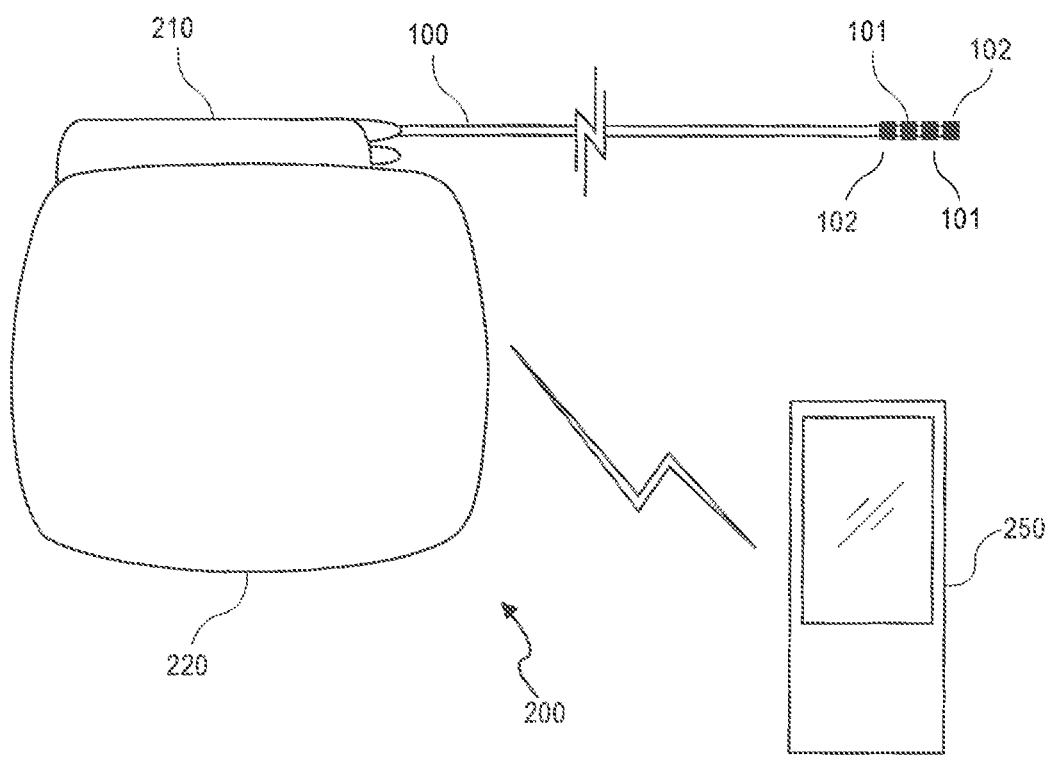
FIG. 2 depicts a system for deep brain stimulation according to some embodiments.

FIG. 2 depicts neurostimulation system 200 according to some embodiments. Neurostimulation system 200 includes pulse generator 220 and one or more directional leads 100. Examples of pulse generators include the BRIO™ and INFINITY™ pulse generators manufactured by Abbott (Plano, TX). Pulse generator 220 is typically implemented using a metallic housing that encloses circuitry for generating the electrical pulses for application to neural tissue of the patient. Control circuitry, communication circuitry, and a non-rechargeable or a rechargeable battery (not shown) are also typically included within pulse generator 220. Pulse generator 220 is usually implanted within a subcutaneous pocket created under the skin by a physician.

Lead 100 is electrically coupled to the circuitry within pulse generator 220 using header 210. Lead 100 includes terminals (not shown) that are adapted to electrically connect with electrical connectors (e.g., "Bal-Seal" connectors which are commercially available and widely known) disposed within header 210. The terminals are electrically coupled to conductors (not shown) within the lead body of lead 100. The conductors conduct pulses from the proximal end to the distal end of lead 100. The conductors are also electrically coupled to electrodes 101 and 102 to apply the pulses to tissue of the patient.

The use of segmented electrodes 101 in system 200 permits the clinician to more precisely control the electrical field generated by the stimulation pulses and, hence, to more precisely control the stimulation effect in surrounding tissue. One or more of electrodes 101 and 102 may be additionally or alternatively utilized to sense electrical activity at the implant location for some embodiments where generator 220 includes suitable sensing circuitry.

Pulse generator 220 preferably wirelessly communicates with programmer device 250. Programmer device 250 enables a clinician to control the pulse generating operations of pulse generator 220. The clinician can select electrode combinations, pulse amplitude, pulse width, frequency parameters, and/or the like using the user interface of programmer device 250. The parameters can be defined in terms of "stim sets," "stimulation programs," (which are known in the art) or any other suitable format. As used herein, a "stimulation program" refers to one or more sets of stimulation parameters that permit a pulse generator to provide a neurostimulation therapy to a patient. Programmer device 250 responds by communicating the parameters to pulse generator 220 and pulse generator 220 modifies its operations to generate stimulation pulses according to the communicated parameters. Any suitable wireless communication method may be used for communications between programmer device 250 and pulse generator 220 such as near field inductive communication and any suitable various far field communication method. For example, the INFINITY™ deep brain stimulation system of Abbott uses BLUETOOTH™ low energy for communication with an implanted pulse generator. Programmer device 250 includes various hardware components such as a display (e.g., a touch screen), one or more user input buttons, battery, processor, memory, wireless communication circuitry, interface components, etc. Commercially available devices may be employed for the hardware components of programmer device 250 such as APPLE IOS IPAD™ devices.

Programmer device 250 includes software (one or more "apps") that provides one or more user interface screens to permit a clinician to identify one or more suitable or optimal deep brain stimulation programs for a given patient and to program pulse generator 220 according to the identified program(s).

Figure 3:
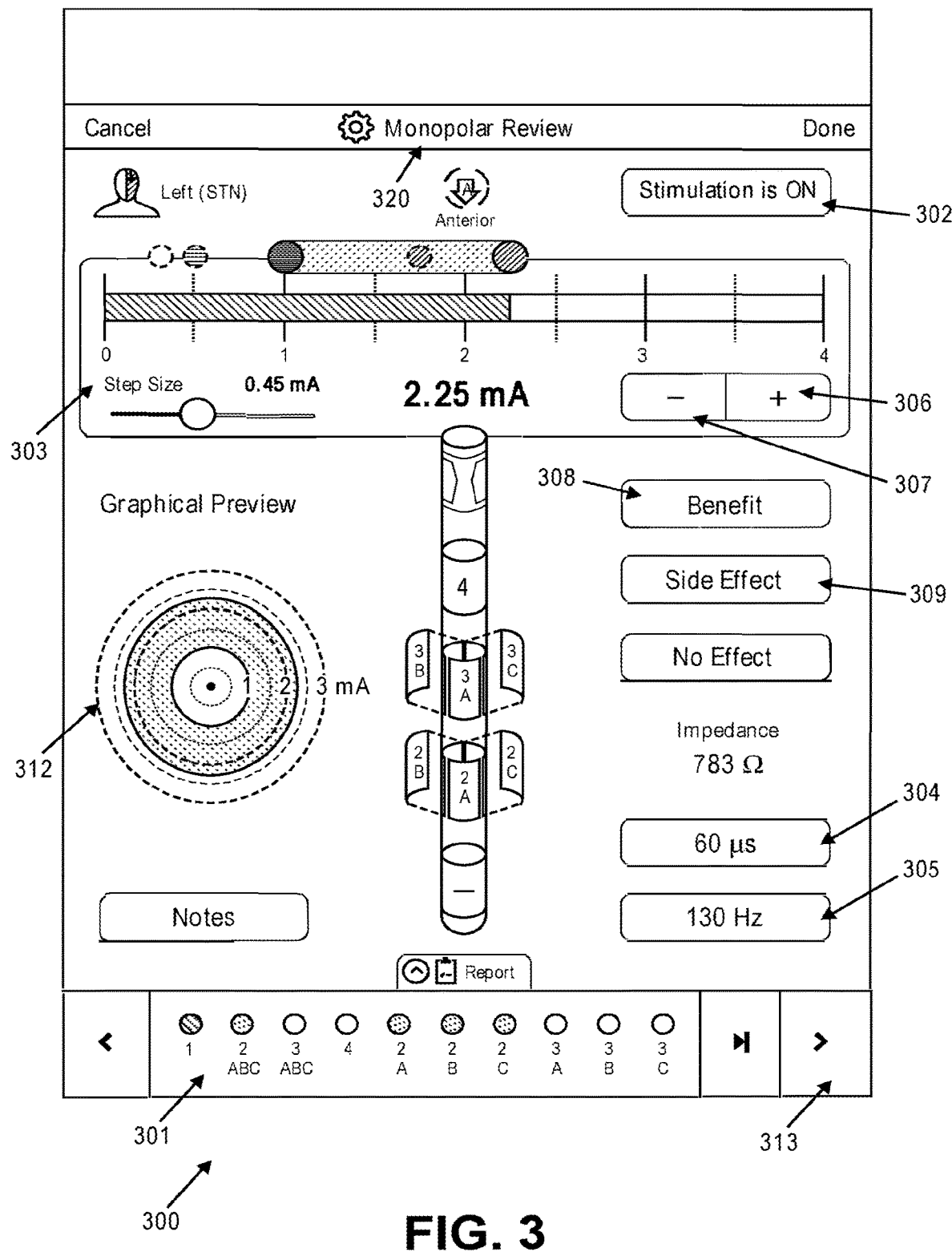
FIG. 3 depicts a user interface screen for conducting a screening review of electrodes for a DBS therapy for a patient according to some embodiments.

FIG. 3 depicts a user interface screen 300 that includes various graphical user interface components for conducting a monopolar review. A monopolar review refers to a programming session in which deep brain stimulation is applied to a patient using various electrode combinations and stimulation parameters. The review is "monopolar" because each active electrode of the stimulation lead has a negative polarity during application of stimulation pulses and the pulse generator case is used as the return electrode (positive polarity). Although monopolar review is described for some embodiments, other embodiments may employ multipolar electrode configurations.

UI screen 300 permits the clinician to apply electrical stimulation at different amplitudes for the various electrode and electrode combinations to identify amplitudes for relevant patient responses. For example, the clinician may determine for each electrode or electrode combination the amplitude value that causes an expected complete benefit for the stimulation therapy (such as elimination of tremor). Also, the clinician may likewise determine the value that causes a sustained side effect (e.g., tingling, tightening, mood changes, or flashing). After an appropriate number of electrodes or combinations have been tested, the clinician may review the recorded data on programming device 250 or elsewhere to select or create an optimal DBS program for the patient. The optimal DBS program may commonly include identification of one or more active electrodes, pulse frequency, pulse width, and pulse amplitude parameters.

UI screen 300 provides an efficient workflow progression for the monopolar review. The clinician may test through a progression of electrodes and/or electrode combinations without necessarily leaving the single screen. Also, UI screen 300 permits the automatic capture of the relevant data without leaving the single screen. The arrangement of GUI components with interrelated functionality permits the relatively complex task of completing a monopolar review to occur with a minimal burden on the clinician.

UI screen 300 includes icon 320 that may be used to start a monopolar review session. The clinician may tap icon 320. If the clinician selects to start a monopolar review session, the current program (if valid) is saved and the monopolar workflow process begins in which the clinician may progress through the various electrodes and electrode combinations. The clinician may select the respective stimulation lead for the monopolar review (e.g., select between the leads implanted on the right and left hemispheres of the patient).

UI screen 300 includes electrode progression navigation GUI component 301. GUI component 301 provides a series of electrode selections for the monopolar review. Clinician programmer device 250 automatically guides the clinician through screening of the electrodes/combinations according to the electrodes shown in GUI component 301. When screening of a given electrode or combination is completed, the clinician may proceed to the next defined electrode or combination by selecting the "next" arrow 313 in GUI component 301. After the clinician selects the "next" arrow 313, clinician programmer device 250 automatically changes the active electrodes by communicating with the implantable pulse generator 220 of the patient.

If the clinician wishes to depart from the defined order, the clinician may select other GUI components associated with a specific electrode or electrode combination. For example, the clinician may select one of the electrodes in the depiction of the directional lead to screen the selected electrode. Also, GUI component 301 includes radio button elements that permit the clinician to provide test stimulation for a specific electrode and/or electrode combination. In FIG. 3, GUI component 301 includes radio button elements 1-4. In option 1, the ring electrode 1 (the most distal electrode) is active for the test stimulation. In option 2 ABC, all segmented electrodes on the second most distal level are active for the test stimulation. In option 3 ABC, all segmented electrodes on the third most distal level are active for the test stimulation. In options 2 ABC and 3 ABC, the individual segmented electrodes at each level are identified as segmented electrodes A, B, and C respectively. When all of the segmented electrodes are active at a given level, the stimulation field is generally extended in a 360 degree manner about the lead. In option 4, the most proximal ring electrode is active for the test stimulation. One specific electrode progression in shown in FIG. 3. Other electrode progressions for screening are described herein. A given electrode progression need not include all possible electrode options. For example, when the clinician finishes screening of a first electrode progression of several electrodes/combinations, UI screen 300 may present a second electrode progression. The specific order or contents of the second electrode progression may depend upon the patient response data obtained during screening of the first electrode progression according to some embodiments.

GUI component 301 includes additional options for individual segmented electrodes which are shown as options 2 A, 2 B, 2 C, 3 A, 3 B, and 3 C. For each of these options, the identified segmented electrode (either electrode A, B, or C) on levels 2 or 3 are active.

In some embodiments, the clinician may select a specific electrode or electrode combination deemed more likely to result in an optimal DBS program. For example, the clinician may believe that a specific electrode is more likely located in an optimal location for deep brain stimulation. This may be based on imaging and/or intraoperative microelectrode recording (MER) data or any other suitable clinical information. If the clinician decides to begin with a specific electrode or combination, the clinician may provide input corresponding to the desired electrode or electrode combination.

As the clinician completes screening for a given electrode or electrode combination, GUI component 301 may be updated to reflect the completion status for the electrode or electrode combination (e.g., the color of the corresponding radio button is changed). If the clinician does not intentionally modify the screening order, programming device 250 will automatically proceed through the screening according to the order specified by the defined electrode progression (in response to the clinician selecting the "next" GUI element of GUI component 301).

User interface screen 300 includes GUI components 302-305 to control the test stimulation applied during analysis of the patient response to stimulation by a given electrode or electrode combination. GUI components 304 and 305 permit the clinician to control the pulse width and pulse frequency for the deep brain stimulation. GUI components 304 and 305 may allow the clinician to enter the desired values via text entry, through selection from a set of values, or any other suitable entry method. These DBS parameters are generally not varied across different electrodes during a monopolar review although there is occasionally some variation in these parameters among different patients. The pulse amplitude and the electrode configuration are the DBS parameters that are commonly analyzed during a monopolar review session to arrive at an optimal DBS therapy.

When the clinician begins a screening session or when the clinician transitions to the next electrode or electrode combination, programmer device 250 communicates with implantable pulse generator 220 to set the electrodes to the appropriate states (e.g., communicates the defined electrode configuration). The electrode or electrodes in the electrode combination are set to active and all other electrodes of the lead are set to neutral for a monopolar review. The case of the IPG is used as the return electrode. As used herein, an electrode configuration refers to the set of electrode states for an electrode combination under test. The electrode configuration may include one active electrode or multiple active electrodes. Also, the initial amplitude is set to zero or a suitable minimum amount. The clinician may select an amplitude step size in GUI component 303. As shown in FIG. 3, constant current pulses are applied and hence the pulse amplitude is given in milliamperes. Voltage pulses may be employed for other embodiments and the pulse amplitude in such cases is a voltage value. The clinician may turn stimulation on by an initial selection of button 306. When stimulation is turned on for a given electrode or electrode combination, the amplitude begins at zero or a suitable minimum value. The clinician may then increase or decrease the pulse amplitude using buttons 306 and 307 of GUI component 303 respectively. The amplitude is increased or decreased according to the amplitude step size for each touch or other selection of buttons 306 and 307. As the clinician modifies the amplitude, the clinician observes or otherwise monitors the patient response and provides additional input to UI screen 300 to record or document the patient response.

When the clinician modifies the pulse amplitude via buttons 306 and 307, programmer device 250 communicates a suitable signal to the pulse generator 220 to modify the pulse amplitude. Pulse generator 220 applies stimulation according to the current deep brain stimulation parameters (pulse frequency, pulse width, and pulse amplitude) displayed in UI interface 300 via the current electrode or electrode combination. During the analysis of a given electrode or electrode combination, pulse generator 220 continuously or substantially continuously applies stimulation while the amplitude is gradually increased according to the selected step size. As used herein, substantially continuous stimulation (or equivalently stimulation without substantial interruption) means stimulation without interruption for one second or more.

As the clinician increases amplitude, the patient response will likely change. The clinician may use UI screen 300 to record when a specific patient response occurs at an identified pulse amplitude. The clinician may indicate when the patient experiences an initial beneficial therapeutic response (e.g., a beneficial change in a respective movement disorder symptom). For example, the patient may more easily perform a bodily movement or the patient's tremor is reduced or eliminated. The clinician may indicate the amplitude at which a partial beneficial response occurs. Also, the clinician may indicate the pulse amplitude at which a complete benefit for a given neurological symptom occurs. The clinician may indicate at which amplitude a transient side effect is experienced and may indicate at which amplitude a sustained side effect is experienced. Depending upon the neurological disorder and/or clinician preferences, multiple types of benefits may be defined and multiple side effects may be defined for identification via UI screen 300.

The recording of the relevant amplitudes for benefits and side effects may occur by touch of buttons 308 and 309 respectively. When the clinician selects one of buttons 308 and 309, a pop over dialog component may be displayed to capture additional information. FIG. 4 depicts dialog component 400 for capturing benefit information. FIG. 5 depicts dialog component 500 for capturing side effect information. The clinician may enter text notations to provide additional information related to a given amplitude value for a benefit or side effect if deemed appropriate by the clinician.

When the clinician identifies a relevant amplitude using these buttons, the amplitude is stored with a suitable identification (partial benefit, complete benefit, transient side effect, or sustained side effect). The amplitude values are stored for subsequent review by the clinician to facilitate identification an optimal DBS program.

UI screen 300 modifies its display as the amplitude values for relevant benefits and side effects are identified by the clinician. The respective identified amplitudes are displayed using markers 311 shown above the amplitude control component 310. UI screen 300 includes graph 312 that depicts the various amplitudes for one or more electrodes. For a ring electrode as shown in FIG. 3, the identified amplitudes are shown as concentric rings with diameters defined by the respective amplitude values. For segmented electrodes, the identified amplitudes may be shown as points at distances defined by the respective amplitude values and positioned proximate to each corresponding segmented electrode. Graph 312 for the segmented levels may connect the corresponding amplitudes for each segmented electrode with lines or suitable curves. For example, lines may connect the amplitude values for the compete benefit points for each adjacent segmented electrode.

In some embodiments, programmer device 250 automatically performs one or more operations when the clinician identifies a side effect by tapping or touching button 309. Programmer device 250 records the current pulse amplitude as the identified amplitude for the side effect. To avoid continuous stimulation of the patient at a level causing a sustained side effect, programmer device 250 automatically decreases the pulse amplitude by the step size by selection of button 309 according to some embodiments. Programmer device 250 communicates a suitable message through its wireless communication circuitry to pulse generator 220 to modify the pulse amplitude of the current DBS program. The stimulation continues without substantial interruption but at an amplitude just below the level at which the side effect was experienced. In some embodiments, programmer device 250 modifies amplitude control component 310 to include a green portion up to the current amplitude value (after the automatic downward adjustment) and to include a dark grey portion from the end of the green portion up to the amplitude at which the side effect was experienced by the patient. By performing these operations automatically, the amount of discomfort experienced by the patient is minimized without requiring additional actions by the clinician and without compromising the integrity of the recorded data.

As previously noted, the clinician may perform an analysis for each electrode or electrode combination in the order listed in UI screen 300. As the clinician analyzes the patient response for a specific electrode and electrode combination, programmer device 250 may suggest that no further testing is likely to lead to a substantially better DBS program based on the data collected at that point. Also, programmer device 250 may suggest progression to a specific electrode or electrode combination or may suggest skipping a specific electrode or electrode combination based on the data collected at that point. Programmer device 250 may provide different electrode progressions at certain transition points depending upon the collected patient response data.

Figure 6:
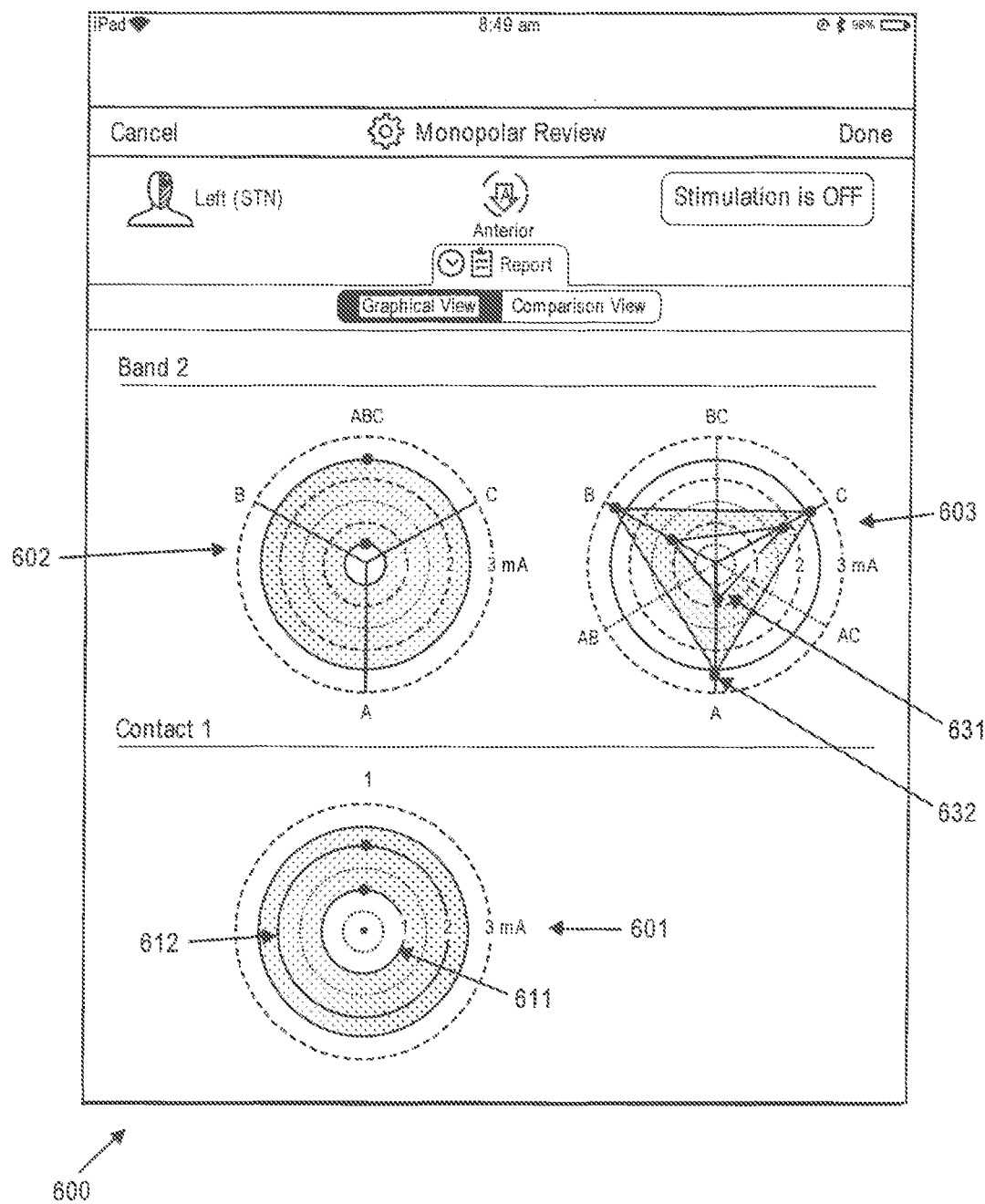
FIGS. 6 and 7 depict graphical representations of patient response data according to some embodiments.

When the clinician completes testing of relevant electrodes and electrode combinations or at any suitable time, the clinician may view automatically generated reports for the completed monopolar review data. FIG. 6 depicts report 600 that includes graphical components for the monopolar review data. Graph 601 represents the data from the analysis of stimulation applied to ring electrode of contact 1. Graph 601 depicts respective concentric circles which include a representation 611 of the amplitude level at which a complete benefit was identified and a representation 612 of the amplitude level at which a sustained side effected was identified. Graph 602 is similar to graph 601 and graph 602 represents the recorded data when all of the segmented electrodes of band 2 are active. Graph 603 represents the recorded data for the individual segmented electrodes of band 2. For example, point 631 represents the identified amplitude for a complete benefit for segmented electrode A of band 2 and point 632 represents the identified amplitude for a sustained side effect for the same segmented electrode. The data points for each segmented electrode in graph 603 are connected by lines for clarity of the graph although any suitable graphical representation may be alternatively employed.

The amplitudes between the complete benefit amplitude and the sustained side effect amplitude represents the therapeutic window for a given electrode or electrode combination. In the automatically generated graphical representations of the monopolar data, the size of therapeutic windows are readily recognized by the clinician to aid the clinicians selection of an optimal DBS program.

Figure 7:
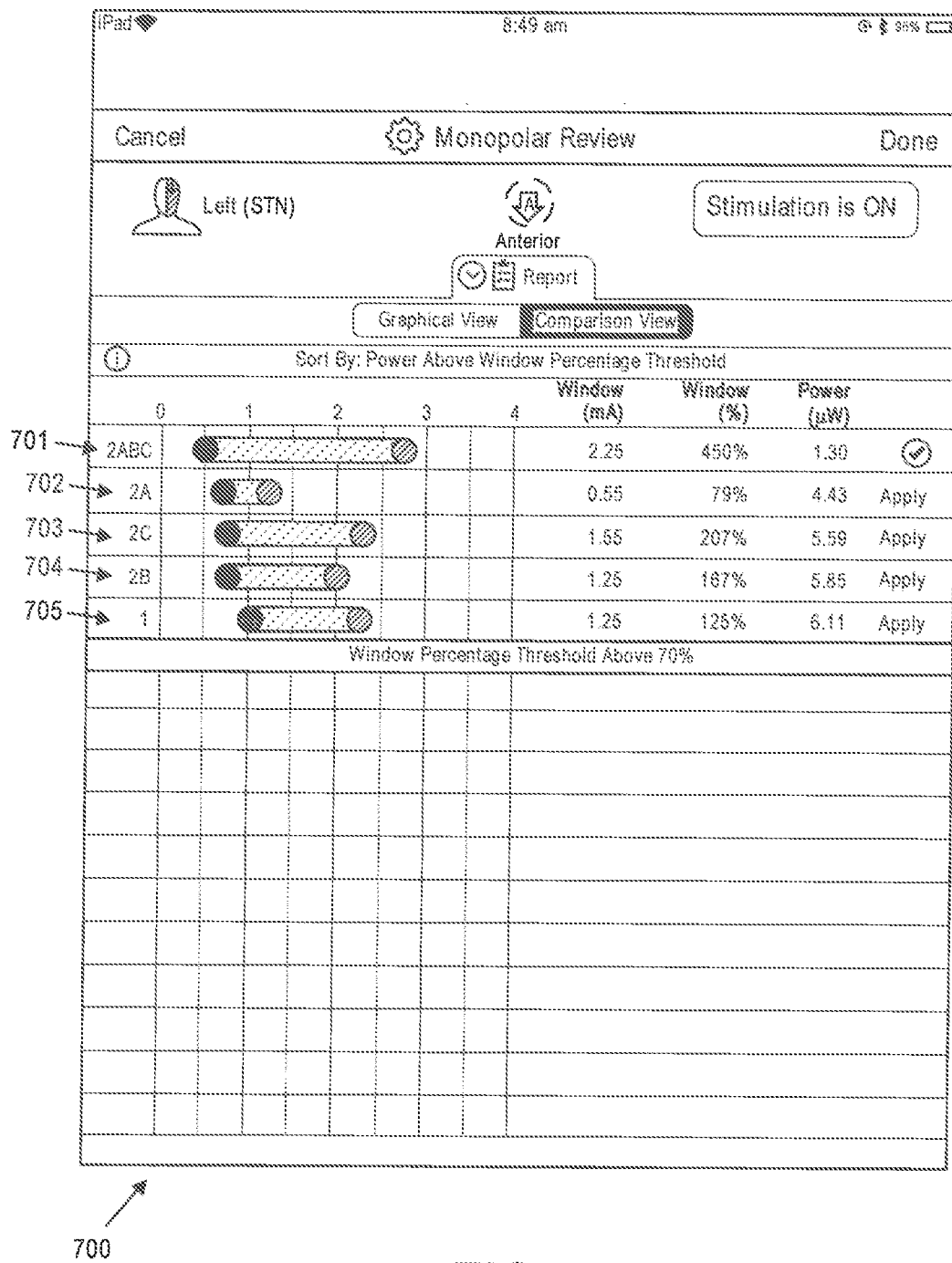

FIG. 7 depicts report 700 that includes graphical components for a comparison view of the monopolar review data. The data points for the various electrodes and electrode combinations are displayed as corresponding graphs 701-705 for this example data set. Each graph 701-705 includes the identified amplitudes for a complete benefit and sustained side effect. The therapeutic window between these values is displayed. Also, data metric values are displayed for each applicable electrode or electrode combination. The window metric is a numerical size of the therapeutic window–the difference (in milliamperes in some embodiments) between the side effect amplitude value and the benefit amplitude value. The window percentage (window %) is the percentage the amplitude may be increased above the benefit threshold before encountering side effects. An equivalent therapeutic window ratio (TWR) metric value (calculated by the window size divided by the recorded benefit amplitude) could be displayed. Higher values for window size are generally preferred for selection of an optimal DBS program. The power metric represents the power required to deliver therapy at the therapy settings. Lower power consumption is generally preferred for selection of an optimal DBS program. The data of report 700 may also be filtered according to some embodiments. For example, electrodes with insufficiently sized therapeutic windows may be excluded and/or with overly taxing power requirements may be excluded.

The display of the monopolar review data in comparison report 700 may be sorted to assist the clinician's selection of an optimal DBS program. For example, the data may be sorted by the therapeutic window ratio (or percentage) metric.

In some embodiments, programmer device 250 automatically defines one or more progressions through electrodes and electrode combinations for testing. The progression may be displayed in navigation GUI component 301 of UI screen 300. When the clinician completes testing of a given electrode, programmer device 250 automatically transitions to the next electrode or electrode combination defined by the respective progression (in response to the clinician selecting button 312 of progression navigation GUI component 301).

Programmer device 250 may define multiple electrode progressions that depend on one or more factors. For example, programmer device 250 may prompt the clinician upon beginning a screening session whether a "detailed" screening or a "quick" screening is appropriate for a given patient. Depending upon the input from the clinician, different electrode progressions for the workflow may be selected by the software of programmer device 250 for the review session.

In other embodiments, programmer device 250 may prompt the clinician to identify an electrode or electrode level that is a more likely candidate for the final DBS program(s). The clinician may make this evaluation of the likelihood based upon MER (microelectrode recording data) or any other suitable clinical data related to the implantation location of the electrodes of the lead. Depending upon the identification of such an electrode from the clinician, the electrode progression may differ. In other embodiments, the clinical data (MER data, imaging data, etc.) may be provided directly to device 250 and device 250 will select the initial electrode for the electrode progression for the session workflow.

Also, programmer device 250 may employ multiple progressions in series. The clinician may proceed through multiple progressions for a single screening session. During an individual session, the next progression may be chosen as a function of data recorded during the prior progression. For example, if a first set of segmented electrodes tested together (for example, 2ABC) produced a therapeutic window of greater size than a second set of segmented electrodes (3ABC), the next progression may start with testing of the individual segmented electrodes of the first set (2A, 2B, 2C) rather than the second set (3A, 3B, 3C).

In some embodiments, programmer device 250 applies one or more evaluations of patient response data to determine whether session testing may be terminated without completing a review of the remaining electrodes. For example, the clinician may define a threshold or target value. The value may be a value for the TWR value that the clinician believes is sufficient to ensure that the patient will experience an effective DBS therapy. If programmer 250 determines that one or more previously tested electrodes or electrode combinations exceed the threshold or otherwise meet appropriate criteria, programmer device 250 may notify the clinician and prompt the clinician to determine how the clinician wishes to proceed. The prompt allows the clinician to interrupt the electrode progression and immediately view session results or to continue with a detailed screening.

FIGS. 8-15 depict respective flows of operations of programmer device 250 to guide the clinician through electrode screening. The operations shown in these FIGS. may be implemented using suitable software code or instructions stored in memory of programmer device 250. The software code may be included within one or more apps defined for the monopolar review or other implantable stimulation system programming software of device 250.

Figure 12:
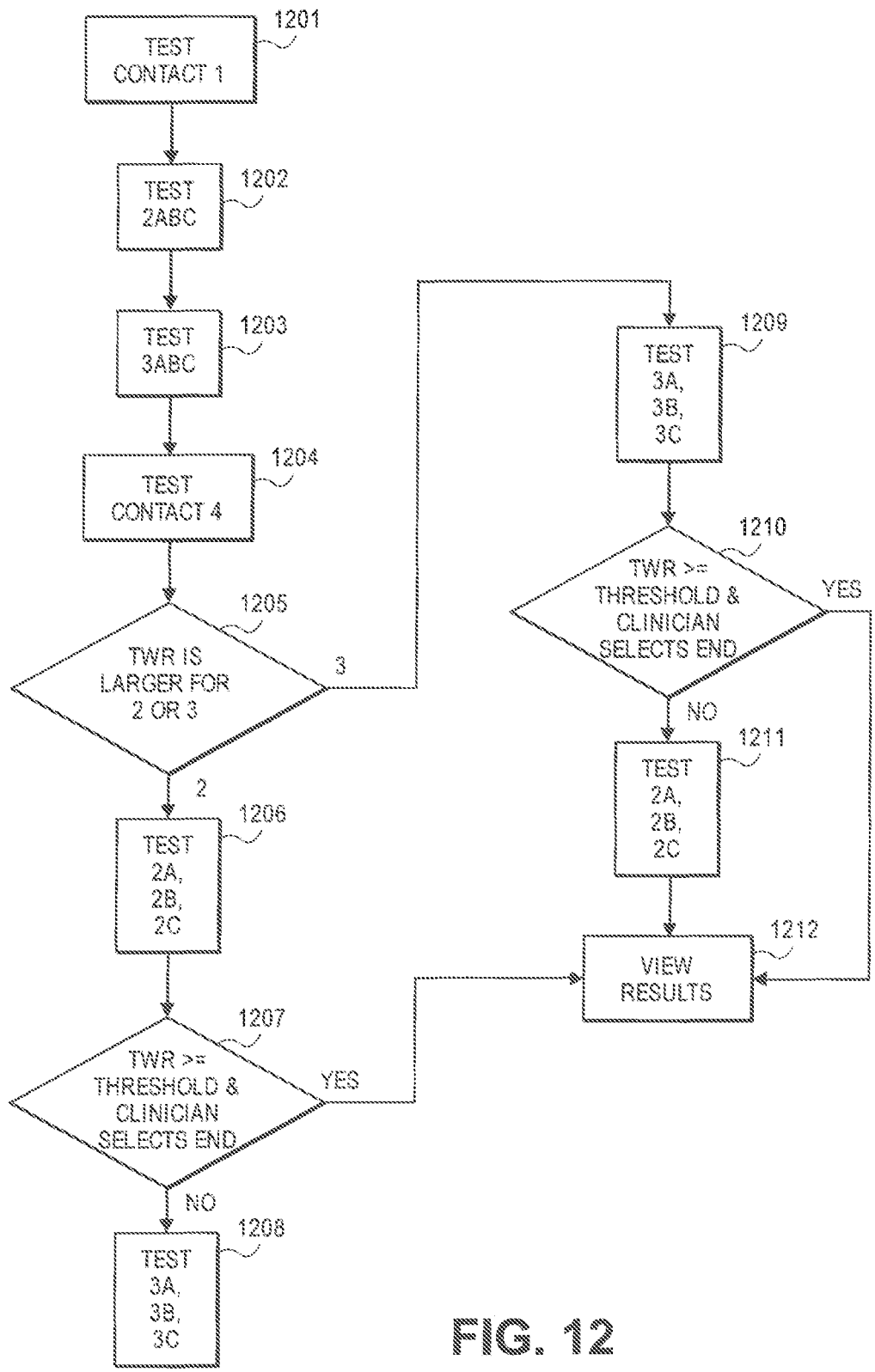

FIG. 12 depicts a flow of operations for conducting a review of electrodes of a DBS lead that includes segmented electrodes according to some representative embodiments. In 1201-1204, the software of device 250 automatically guides the clinician through testing of contacts 1, 2ABC, 3ABC, and contact 4. For "2ABC" and "3ABC", all of the segmented electrodes on the given level are set as active electrodes for delivery of the deep brain stimulation. For each tested electrode, the clinician controls the deep brain stimulation (gradually increasing the pulse amplitude) and observes or otherwise monitors the patient response. The clinician identifies the therapeutic window for each tested electrode/electrode combination by identifying amplitude values for benefit(s) and side effect(s).

At 1205, the software of device 250 completes a logical comparison to determine whether the TWR value is greater for level 2 (2ABC) or for level 3 (3ABC) based on the session data. If TWR value for level 2 is greater, the segmented electrodes for level 2 are tested individually (only one segmented electrode active at a time) at 1206. Otherwise, the process flow proceeds from 1205 to 1209.

At 1207, after the individual segmented electrodes of level 2 were tested, a logical comparison is made to determine whether the TWR for one or more of tested electrodes/combinations is greater than a defined threshold value. If so, the clinician is prompted whether the clinician wishes to continue with more detailed screening or whether to end screening to view the results of the review to this point. If the clinician selects to end, the process flow proceeds to 1212 where the session results are provided to the clinician. For example, report screens 600 and 700 may be displayed to the clinician. If not, the process flow proceeds from 1207 to 1208 where the segmented electrodes for level 3 are tested individually (only one segmented electrode active at a time).

At 1209, the segmented electrodes for level 3 are tested individually (only one segmented electrode active at a time).

At 1210, after the individual segmented electrodes of level 3 were tested, a logical comparison is made to determine whether the TWR for one or more of tested electrodes/combinations is greater than a defined threshold value. If so, the clinician is prompted whether the clinician wishes to continue with more detailed screening or whether to end screening to view the results of the review to this point. If the clinician selects to end, the process flow proceeds to 1212 where the session results are provided to the clinician. If not, the process flow proceeds from 1210 to 1211 where the segmented electrodes for level 2 are tested individually (only one segmented electrode active at a time).

From 1208 and 1211, the process flow proceeds to 1212 where the clinician views session results. In certain other embodiments, additional testing of two segmented electrodes may occur as discussed herein.

FIGS. 8-11 depict respective process flows for session workflows that vary depending upon an initial identification of a more probable electrode (either by the physician or by logic of device 250). As discussed herein, the clinician may identify an electrode or electrode level to begin the session testing based on MER data, imaging data, and/or other relevant clinical data. Each of FIGS. 8-11 begins with a different electrode selection to begin the workflow. The operations discussed in FIGS. 8-11 may be implemented by software operations in clinician programmer device 250 to automatically guide the clinician through a workflow of testing operations.

Figure 8:
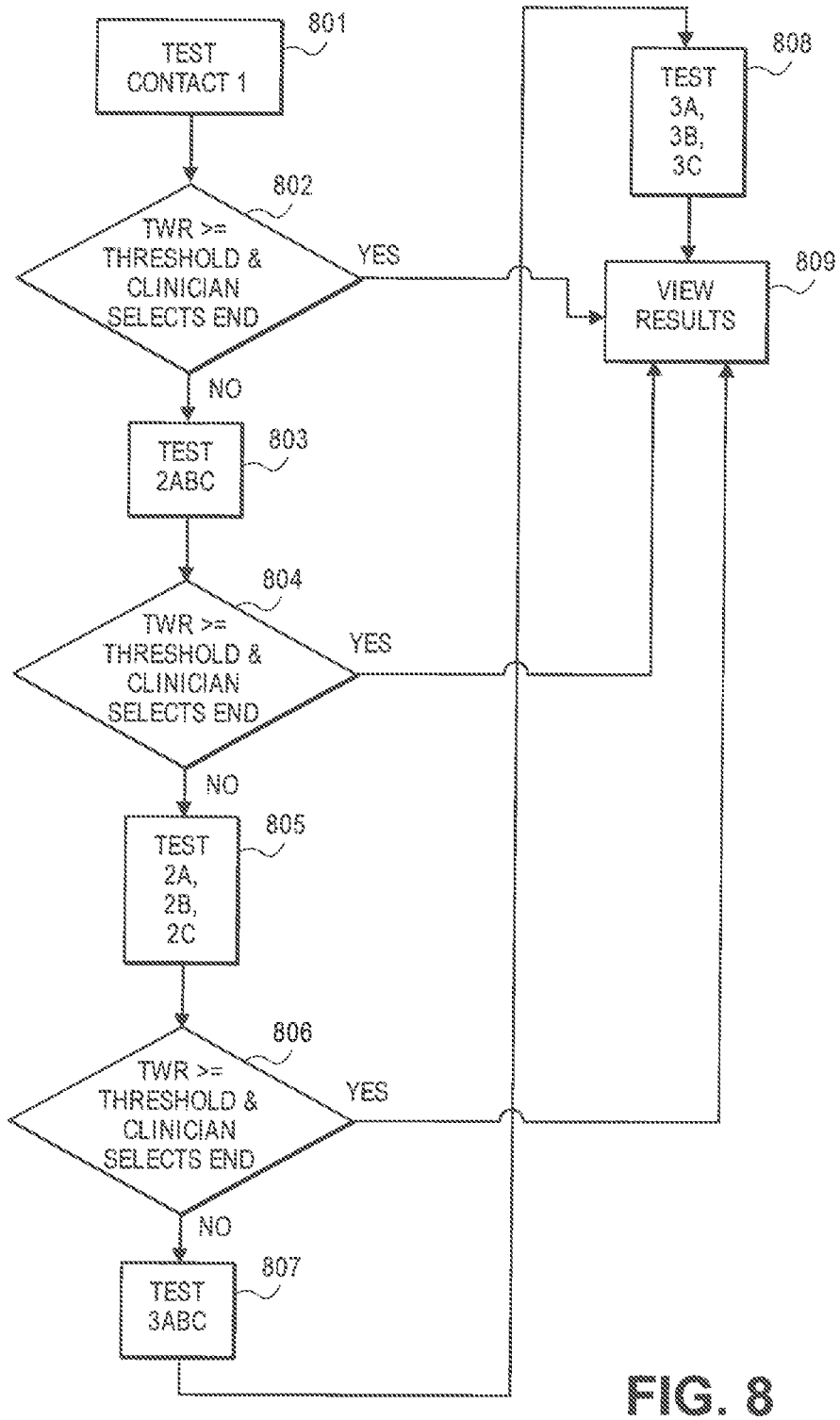
FIGS. 8-15 depict flowcharts of operations for conducting a screening review of electrodes for a DBS therapy for a patient according to some embodiments.

FIG. 8 depicts a flow of operations for conducting a review of electrodes of a DBS lead that includes segmented electrodes according to some representative embodiments.

In 801, contact 1 is tested to determine the therapeutic window as discussed herein. In 802, a logical comparison is made to determine whether the TWR value for the tested electrode is greater than a defined threshold value. If so, the clinician is prompted whether the clinician wishes to continue with more detailed screening or whether to end screening to view the results of the review to this point. If the clinician selects to end, the process flow proceeds to 809 where the session results are provided to the clinician.

In 803, level 2 is tested such that all segmented electrodes on level 2 are set to the active state. The testing determines the therapeutic window. In 804, a logical comparison is made to determine whether the TWR value is greater than a defined threshold value and whether the clinician wishes to end and immediately view the results. If so, the process flow proceeds to 809 where the session results are provided to the clinician.

In 805, each segmented electrode of level 2 is tested with only one segmented electrode set as active at a time. The testing determines the therapeutic window for each segmented electrode. In 806, a logical comparison is made to determine whether the TWR value for any of the segmented electrodes is greater than a defined threshold value and whether the clinician wishes to end and immediately view the results. If so, the process flow proceeds to 809 where the session results are provided to the clinician.

In 807, level 3 is tested such that all segmented electrodes on level 3 are set to the active state. In 808, each segmented electrode of level 3 is tested with only one segmented electrode set as active at a time. At 809, the session results are provided to the clinician.

Figure 9:
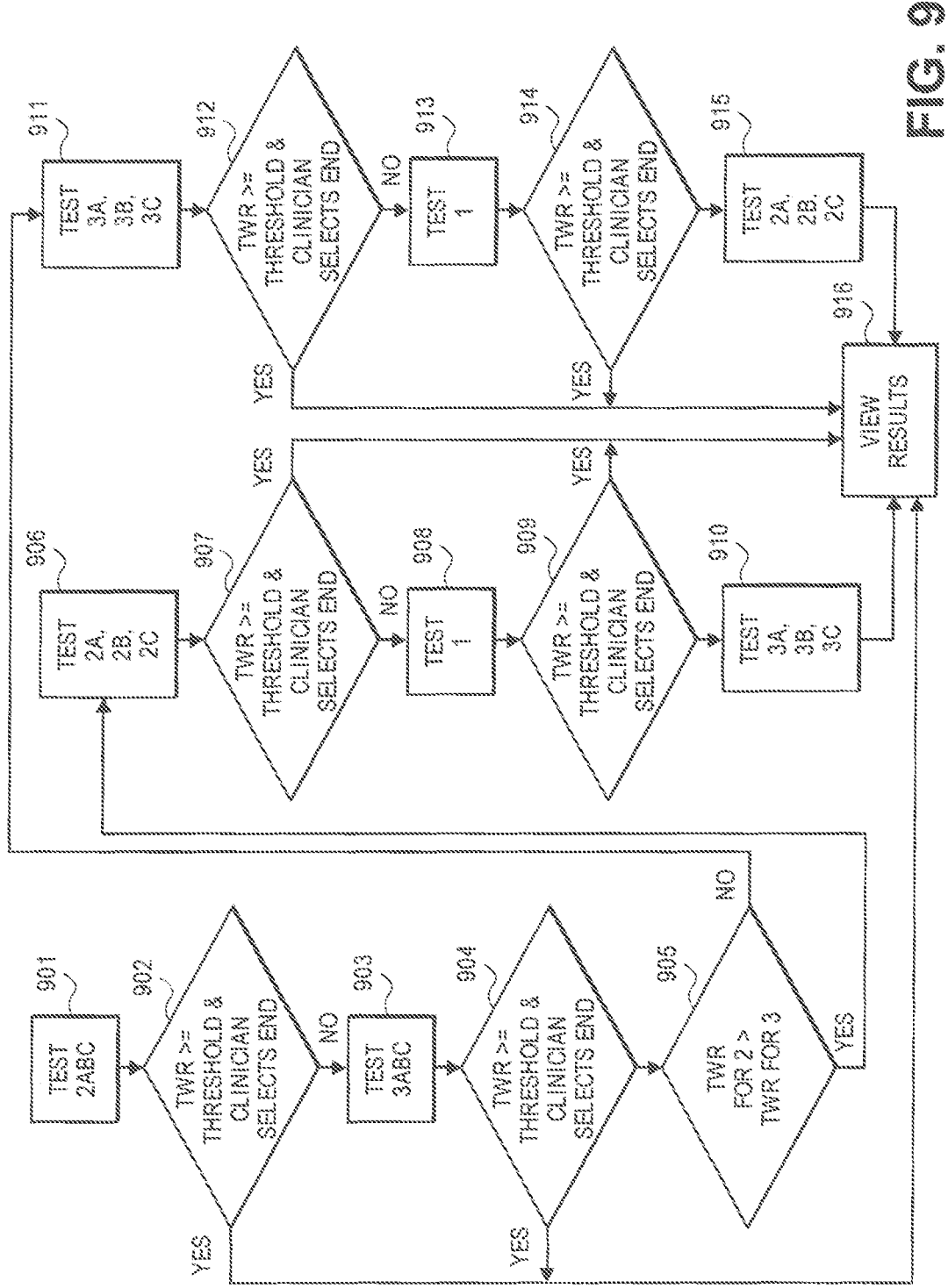

FIG. 9 depicts a flow of operations for conducting a review of electrodes of a DBS lead that includes segmented electrodes according to some representative embodiments. FIG. 9 may be performed when level 2 is identified or selected as the appropriate electrode to begin a review session of a stimulation lead for a patient.

At 901, level 2 is tested such that all segmented electrodes on level 2 are set to the active state. The testing determines the therapeutic window. At 902, a logical comparison is made to determine whether the TWR value is greater than a defined threshold value and whether the clinician wishes to end and immediately view the results. If so, the process flow proceeds to 916 where the session results are provided to the clinician.

At 903, level 3 is tested such that all segmented electrodes on level 2 are set to the active state. The testing determines the therapeutic window. At 904, a logical comparison is made to determine whether the TWR value is greater than a defined threshold value and whether the clinician wishes to end and immediately view the results. If so, the process flow proceeds to 916 where the session results are provided to the clinician.

At 905, a logical comparison is made to determine whether the TWR value for level 2 is greater than the TWR value for level 3. If so, the process flow proceed to 906. If not, the process flow proceeds to 911.

At 906, each segmented electrode of level 2 is tested with only one segmented electrode set as active at a time. The testing determines the therapeutic window for each segmented electrode. In 907, a logical comparison is made to determine whether the TWR value for any of the segmented electrodes is greater than a defined threshold value and whether the clinician wishes to end and immediately view the results. If so, the process flow proceeds to 916 where the session results are provided to the clinician.

In 908, contact 1 is tested to determine the therapeutic window as discussed herein. In 909, a logical comparison is made to determine whether the TWR value is greater than a defined threshold value and whether the clinician wishes to end and immediately view the results. If so, the process flow proceeds to 916 where the session results are provided to the clinician.

In 910, each segmented electrode of level 3 is tested with only one segmented electrode set as active at a time. The process flow proceeds from 910 to 916 where the session results are provided to the clinician.

At 911, each segmented electrode of level 3 is tested with only one segmented electrode set as active at a time. The testing determines the therapeutic window for each segmented electrode. In 912, a logical comparison is made to determine whether the TWR value for any of the segmented electrodes is greater than a defined threshold value and whether the clinician wishes to end and immediately view the results. If so, the process flow proceeds to 916 where the session results are provided to the clinician.

In 913, contact 1 is tested to determine the therapeutic window as discussed herein. In 914, a logical comparison is made to determine whether the TWR value is greater than a defined threshold value and whether the clinician wishes to end and immediately view the results. If so, the process flow proceeds to 916 where the session results are provided to the clinician.

In 915, each segmented electrode of level 2 is tested with only one segmented electrode set as active at a time. The process flow proceeds from 915 to 916 where the session results are provided to the clinician.

Figure 10:
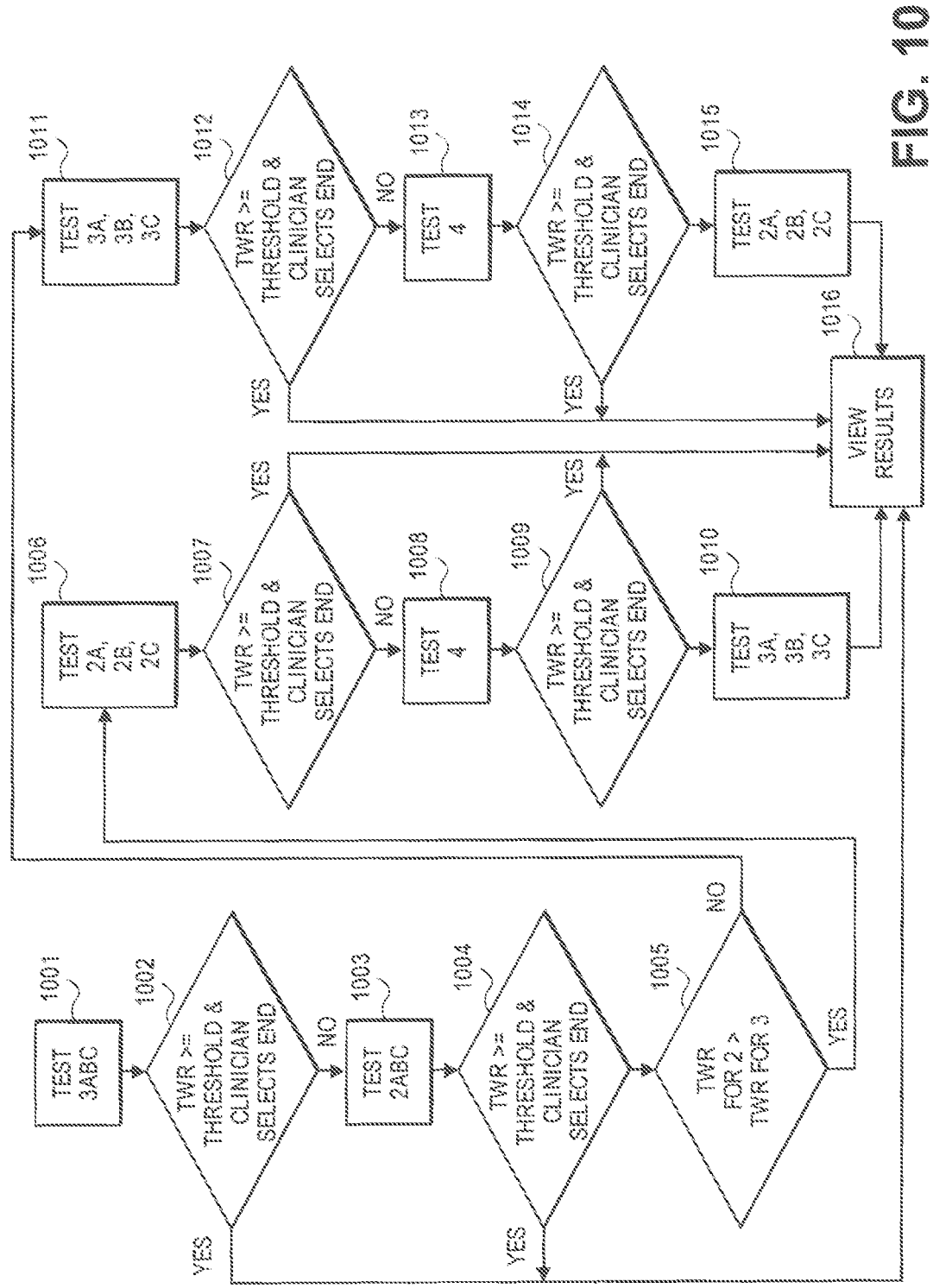

FIG. 10 depicts a flow of operations for conducting a review of electrodes of a DBS lead that includes segmented electrodes according to some representative embodiments. FIG. 10 may be performed when level 3 is identified or selected as the appropriate electrode to begin a review session of a stimulation lead for a patient. The process flow in FIG. 10 of 1001-1016 is similar to the process flow of FIG. 9 except that the process flow of FIG. 10 begins with testing of all of the segmented electrodes of level 3 and the all of the segmented electrodes of level 2. If electrode 3 is identified as the best starting candidate, electrode 4 is more likely to be an optimal selection (after electrode 3). Accordingly, in FIG. 10, electrode 4 is screened and electrode 1 is omitted. The process flow is essentially the same upon bifurcation of the workflow upon the comparison of the TWR values for level 3 and level 2 at 1005 with the exception that contact 4 is screened.

Figure 11:
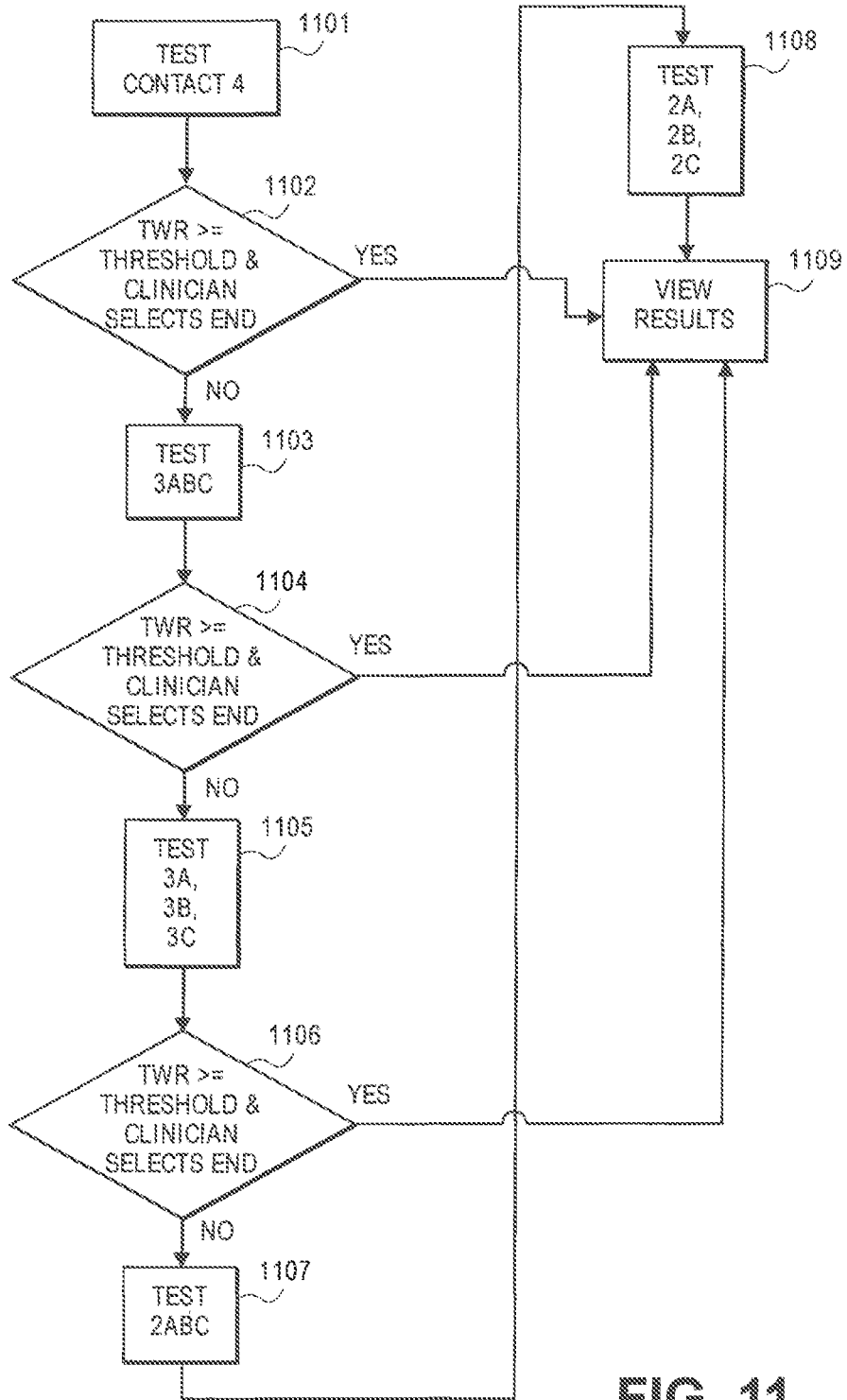

FIG. 11 depicts a flow of operations for conducting a review of electrodes of a DBS lead that includes segmented electrodes according to some representative embodiments. FIG. 11 may be performed when contact 4 is identified or selected as the appropriate electrode to begin a review session of a stimulation lead for a patient.

In 1101, contact 4 is tested to determine the therapeutic window as discussed herein. In 1102, a logical comparison is made to determine whether the TWR value for the tested electrode is greater than a defined threshold value. If so, the clinician is prompted whether the clinician wishes to continue with more detailed screening or whether to end screening to view the results of the review to this point. If the clinician selects to end, the process flow proceeds to 1109 where the session results are provided to the clinician.

In 1103, level 3 is tested such that all segmented electrodes on level 3 are set to the active state. The testing determines the therapeutic window. In 1104, a logical comparison is made to determine whether the TWR value is greater than a defined threshold value and whether the clinician wishes to end and immediately view the results. If so, the process flow proceeds to 1109 where the session results are provided to the clinician.

In 1105, each segmented electrode of level 3 is tested with only one segmented electrode set as active at a time. The testing determines the therapeutic window for each segmented electrode. In 1106, a logical comparison is made to determine whether the TWR value for any of the segmented electrodes is greater than a defined threshold value and whether the clinician wishes to end and immediately view the results. If so, the process flow proceeds to 1109 where the session results are provided to the clinician.

In 1107, level 2 is tested such that all segmented electrodes on level 3 are set to the active state. In 1108, each segmented electrode of level 2 is tested with only one segmented electrode set as active at a time. At 1109, the session results are provided to the clinician.

Figure 13:
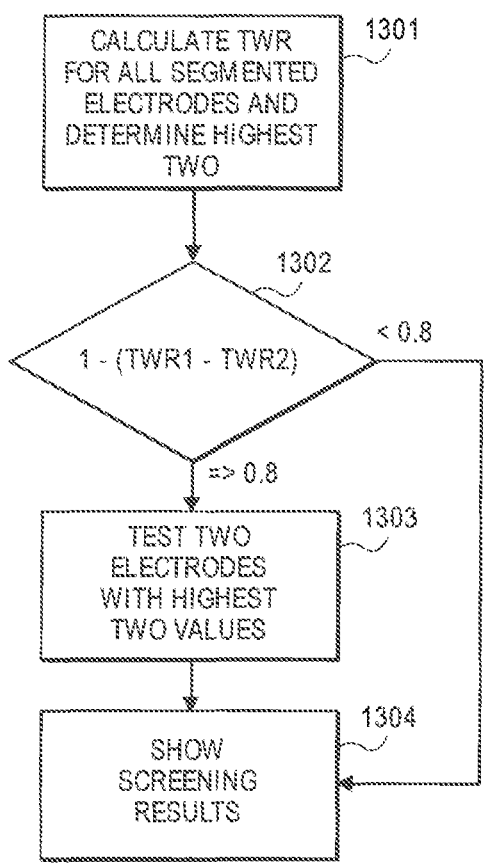

FIG. 13 depicts a flow of operations for conducting a review of electrodes of a DBS lead that includes segmented electrodes according to some representative embodiments. The process flow of FIG. 13 permits additional testing of segmented electrodes if believed appropriate by a clinician. The configuration for screening in FIG. 13 uses a configuration of only two segmented electrodes. The clinician may access this testing option via progression navigation GUI component 301 according to some embodiments.

In 1301, a therapeutic window metric (e.g., the TWR metric) is calculated for the segmented electrodes of the DBS lead. The segmented electrodes with the highest metric values are identified (denoted by TWR1 for the highest value and TWR2 for the second highest value). In 1302, a logical comparison is made based on the TWR1 and TWR2 values. If the value of 1−(TWR1−TWR2) is less than 0.8 or another suitable value, the process flow proceeds from 1302 to 1304 where the screening results are displayed. If the value of 1−(TWR1−TWR2) is greater than or equal to 0.8 or another suitable value, the process flow proceeds from 1302 to 1303. In 1303, the two segmented electrodes exhibiting these values are set as active electrodes and subjected to screening to determine the therapeutic window for these electrodes. In 1304, the screening results are provided to the clinician including the results of the screening of the segmented electrodes for the TWR1 and TWR2 values (both of these segmented electrodes simultaneously set as the active electrodes).

Figures 14, 15:
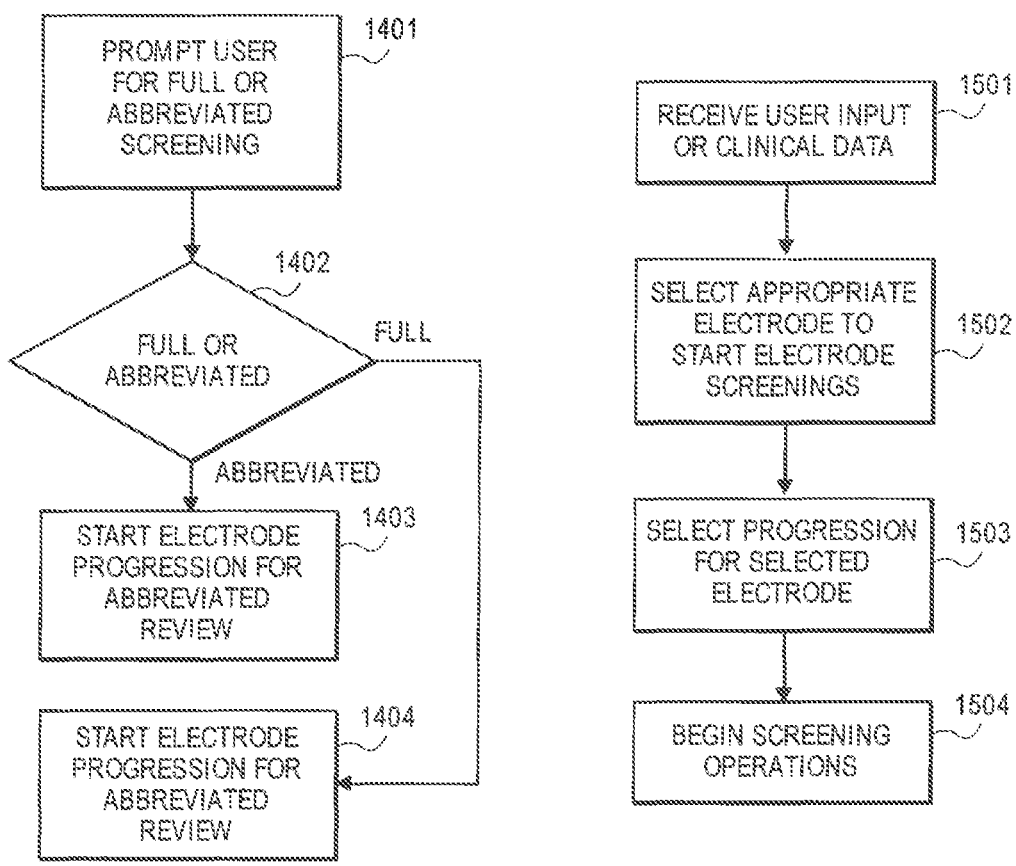

FIG. 14 depicts a flow of operations for conducting a review of electrodes of a DBS lead that includes segmented electrodes according to some representative embodiments.

In 1401, clinician programmer 250 prompts the clinician user whether the user wishes to conduct a full screening review or an abbreviated screening review. In response the received user input, a logical comparison is made in 1402. If the user indicated abbreviated screening, the process flow proceeds to 1403. An abbreviated screening review may be performed in which screening one or more electrodes may be omitted. The omission of screening of certain electrodes may depend upon patient response data that is received. The electrode progressions and the logic for proceeding to electrodes and omitting screening of electrodes may be performed according to any suitable manner including the work flows described herein. If the user wishes to conduct a full screening, the process flow proceeds from 1402 to 1404 where a suitable screening review occurs.

FIG. 15 depicts a flow of operations for conducting a review of electrodes of a DBS lead that includes segmented electrodes according to some representative embodiments. In 1501, user input or clinical data is received by programmer device 250. In 1502, the initial electrode is selected based on the input or the received clinical data. The user input may directly identify an appropriate electrode or electrode level to begin a screening session. Alternatively, clinical data may be received. For example, MER recording data and/or imaging data may be received which may be process to identify an appropriate electrode or electrode level. For example, Lozano discloses identifying locations within the brain for targeting for DBS based on analysis of MER data in U.S. Patent App. Pub. No. 201000204748 entitled "Identifying areas of the brain by examining the neuronal signals," which is incorporated herein by reference. Analysis of MER data at respective locations against appropriate signal characteristics (spiking rates, frequency content, boundary conditions) from an implant procedure and comparison to electrode locations may be employed to select the electrode or electrode level for screening. In 1503, an electrode progression is selected based on the selected electrode or electrode level. In 1504, electrode screening operations begin based on the selected electrode progression.

Figure 16:
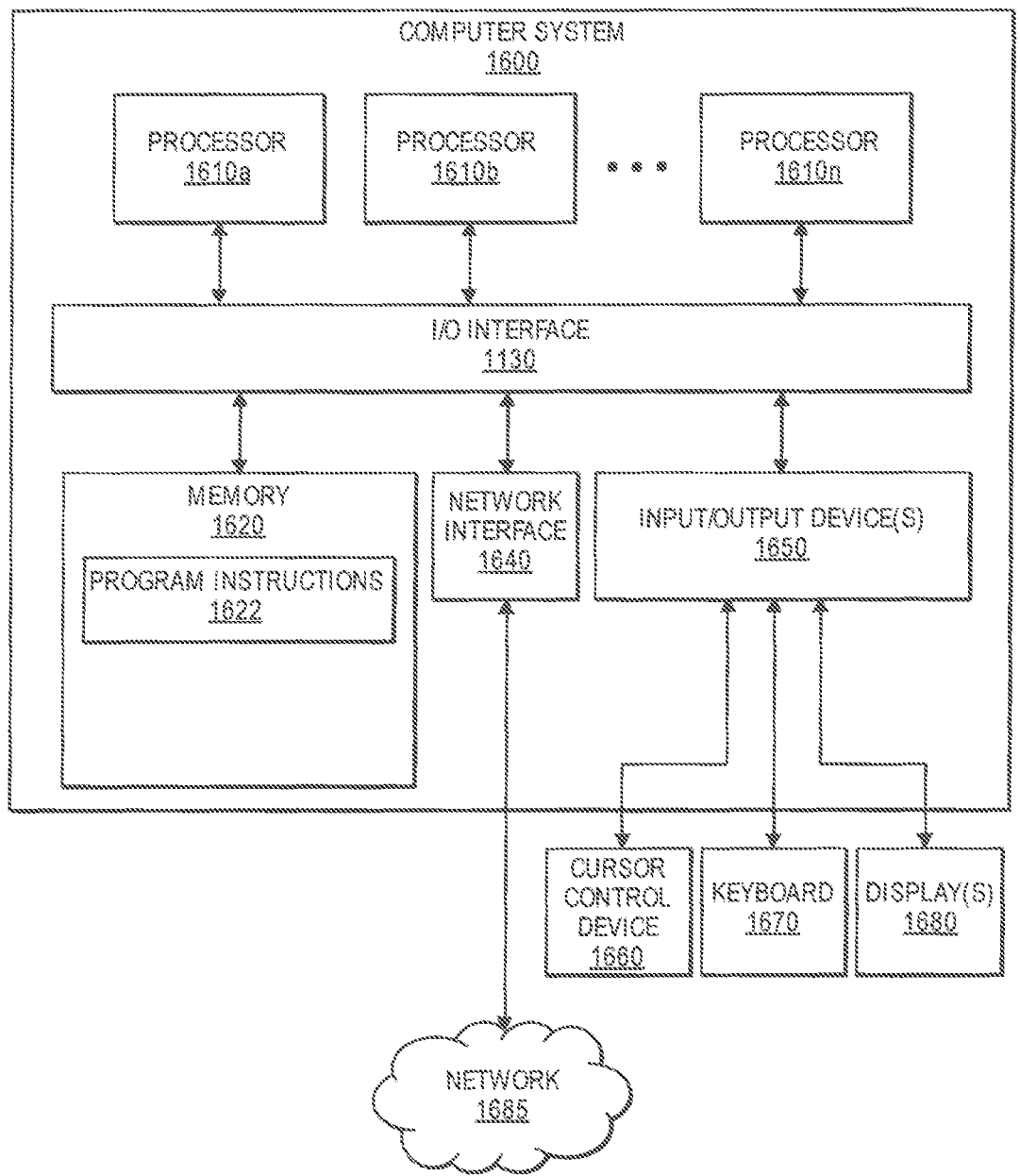
FIG. 16 depicts a clinician programmer device according to some embodiments.

FIG. 16 illustrates an example computer system 1600 that may be configured to include or execute any or all of the embodiments described above. In different embodiments, computer system 1600 may be any of various types of devices, including, but not limited to, a personal computer system, desktop computer, laptop, notebook, tablet, slate, pad, or netbook computer, cell phone, smartphone, PDA, portable media device, handheld computer, or a mobile device.

Various embodiments of a clinician programmer for a deep brain stimulation system, as described herein, may be executed in one or more computer systems 1600, which may interact with various other devices. In some embodiments, computer system 1600 includes one or more processors 1610 coupled to a system memory 1620 via an input/output (I/O) interface 1630. Computer system 1600 further includes a network interface 1640 coupled to I/O interface 1630, and one or more input/output devices 1650, such as cursor control device 1660, keyboard 1670, and display(s) 1680.

In various embodiments, computer system 1600 may be a uniprocessor system including one processor 1610, or a multiprocessor system including several processors 1610 (e.g., two, four, eight, or another suitable number). Processors 1610 may be any suitable processor capable of executing instructions. For example, in various embodiments processors 1610 may be general-purpose or embedded processors implementing any of a variety of instruction set architectures (ISAs), such as the x86, PowerPC, SPARC, or MIPS ISAs, or any other suitable ISA. In multiprocessor systems, each of processors 1610 may commonly, but not necessarily, implement the same ISA.

System memory 1620 may be configured to store clinician programming software instructions or code 1622 accessible by processor 1610. In various embodiments, system memory 1620 may be implemented using any suitable memory technology, such as static random access memory (SRAM), synchronous dynamic RAM (SDRAM), nonvolatile/Flash-type memory, or any other type of memory. In some embodiments, software instructions 1622 may be configured to implement one or more of the work flows described herein and/or provide one or more of the user interface screens described herein. Additionally, program instructions 1622 of memory 1620 may include any of the information or data structures described above. In some embodiments, program instructions and/or data may be received, sent or stored upon different types of computer-accessible media or on similar media separate from system memory 1620 or computer system 1600. While computer system 1600 is described as implementing the functionality of functional blocks of previous Figures, any of the functionality described herein may be implemented via such a computer system.

In one embodiment, I/O interface 1630 may be configured to coordinate I/O traffic between processor 1610, system memory 1620, and any peripheral devices in the device, including network interface 1640 or other peripheral interfaces, such as input/output devices 1650. In some embodiments, I/O interface 1630 may perform any necessary protocol, timing or other data transformations to convert data signals from one component (e.g., system memory 1620) into a format suitable for use by another component (e.g., processor 1610). In some embodiments, I/O interface 1630 may include support for devices attached through various types of peripheral buses, such as a variant of the Peripheral Component Interconnect (PCI) bus standard or the Universal Serial Bus (USB) standard, for example. In some embodiments, the function of I/O interface 1630 may be split into two or more separate components, such as a north bridge and a south bridge, for example. Also, in some embodiments some or all of the functionality of I/O interface 1630, such as an interface to system memory 1620, may be incorporated directly into processor 1610.

Network interface 1640 may be configured to allow data to be exchanged between computer system 1600 and other devices attached to a network 1685 (e.g., carrier or agent devices) or between nodes of computer system 1600. Network 1685 may in various embodiments include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 1640 may support communication via wired or wireless general data networks.

Input/output devices 1650 may, in some embodiments, include one or more display terminals, keyboards, keypads, touchpads, scanning devices, voice or optical recognition devices, or any other devices suitable for entering or accessing data by one or more computer systems 1600. Multiple input/output devices 1650 may be present in computer system 1600 or may be distributed on various nodes of computer system 1600. In some embodiments, similar input/output devices may be separate from computer system 1600 and may interact with one or more nodes of computer system 1600 through a wired or wireless connection, such as over network interface 1640.

As shown in FIG. 16, memory 1620 may include software instructions 1622, which may be processor-executable to implement any element or action described above. In some embodiments, the software instructions may implement deep brain stimulation programming and electrode screening operations described herein.

Those skilled in the art will appreciate that computer system 1600 is merely illustrative and is not intended to limit the scope of embodiments. In particular, the computer system and devices may include any combination of hardware or software that can perform the indicated functions or operations. Computer system 1600 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. Generally speaking, a computer-accessible medium may include a non-transitory, computer-readable storage medium or memory medium such as magnetic or optical media, e.g., disk or DVD/CD-ROM, volatile or non-volatile media such as RAM (e.g. SDRAM, DDR, RDRAM, SRAM, etc.), ROM, etc.

Figure 17:
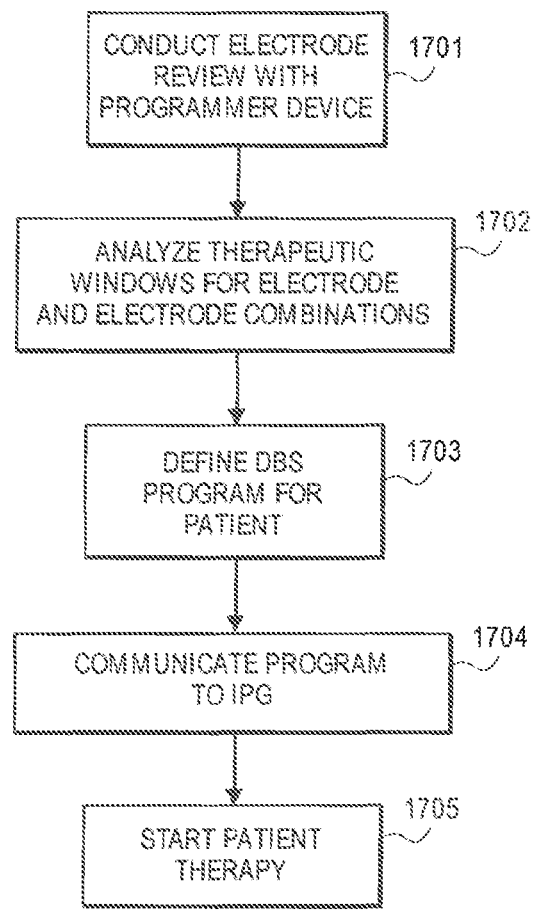
FIG. 17 depicts a flowchart for treating a neurological disorder of a patient using an implantable pulse generator and a lead with segmented electrodes according to some embodiments.

FIG. 17 depicts a flowchart for treating a neurological disorder of a patient using an implantable pulse generator and a lead with segmented electrodes according to some embodiments. In 1701, a clinician conducts an electrode screening review with an appropriate programmer device according to one or more of the embodiments discussed herein. In 1702, the clinician analyzes the therapeutic windows for electrode and electrode combinations from the screening review. In 1703, the clinician defines a DBS program for the patient based on the screening data. For example, the clinician may select an electrode or electrode combination with a suitably large therapeutic window. Also, the clinician may select between suitable electrodes and electrode combinations by considering the power requirements. In 1704, the clinician communicates the DBS program to the patient's IPG. In 1705, the patient's therapy is started by delivering electrical stimulation from the IPG to the patient using one or more directional leads.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A method of controlling delivery of deep brain stimulation to a patient, the method comprising:
    providing, via a display of a clinician programmer device, one or more interface screens for guiding a user through testing of electrode configurations of electrodes of an implantable stimulation lead that is coupled to an implantable pulse generator, wherein the clinician programmer device includes wireless communication circuitry for conducting wireless communications with the implantable pulse generator after implantation within a patient;
    controlling, via wireless communications from the clinician programmer device to the implantable pulse generator, delivery of deep brain stimulation to the patient by the implantable pulse generator, wherein controlling delivery of deep brain stimulation to the patient includes modifying a deep brain stimulation (DBS) pulse amplitude for each tested electrode configuration;
    receiving a first input from a user of the clinician programmer device, wherein the first input includes at least identification of a therapeutic window for one or more DBS parameters for each tested electrode configuration, and wherein the therapeutic window is defined by one or more DBS parameters used for test stimulation for a DBS benefit and a DBS side effect experienced by the patient during testing; and
    responsive to receiving a second input from the user of the clinician programmer device that identifies a side effect experienced by the patient for an electrode configuration under test, controlling delivery of deep brain stimulation to the patient by the implantable pulse generator by automatically decreasing the DBS pulse amplitude associated with the electrode configuration under test.

2. The method of claim 1, wherein automatically decreasing the DBS pulse amplitude includes automatically decreasing the DBS pulse amplitude without substantially interrupting deep brain stimulation of the patient according to the electrode configuration under test.

3. The method of claim 1, further comprising:
    comparing therapeutic windows for each tested electrode configuration to a target value; and
    alerting the user of the clinician programmer device that the target value has been reached, wherein the comparing and alerting are performed by the clinician programmer device.

4. The method of claim 3, further comprising:
    receiving input from the user of the clinician programmer device whether to skip additional electrode screening after the target value has been reached.

5. The method of claim 1, further comprising:
    comparing power requirements associated with therapy thresholds for the tested electrode configuration by the clinician programmer device and informing the user of the clinician programmer device whether each electrode configuration is likely to provide an optimal DBS program for the patient.

6. The method of claim 1, further comprising:
    providing a suggestion message, via the clinician programmer device, to omit testing of one or more electrode configurations based on screening review data previously recorded for the patient.

7. The method of claim 1, further comprising:
displaying, via the display of the clinician programmer device, one or more graphical user interface components depicting respective therapeutic window data for tested electrode configurations.

8. The method of claim 7, further comprising receiving input data from the user, via the clinician programmer device, to filter respective sets of therapeutic window data for tested electrode configurations for presentation to the user of the clinician programmer device.

9. The method of claim 8, further comprising displaying, via the display of the clinician programmer device, filtered therapeutic window data for tested electrode configurations based at least in part on the input data received from the user.

10. The method of claim 7, further comprising receiving input data from the user, via the clinician programmer device, to sort respective sets of therapeutic window data for tested electrode configurations for presentation to the user of the clinician programmer device.

11. The method of claim 10, further comprising displaying, via the display of the clinician programmer device, sorted therapeutic window data for tested electrode configurations based at least in part on the input data received from the user.

12. The method of claim 1, further comprising evaluating therapeutic window parameters for a first set of segmented electrodes and a second set of electrodes.

13. The method of claim 12, further comprising providing information associated with the evaluated therapeutic window parameters, via the display of the clinician programmer device, at the one or more interface screens.

14. The method of claim 12, wherein the evaluating includes omitting screening of one ring electrode depending upon a comparison of the therapeutic window parameters for the first and second sets of segmented electrodes.

15. The method of claim 12, wherein the evaluating includes changing an order of testing individual segmented electrodes depending upon a comparison of the therapeutic window parameters for the first and second sets of segmented electrodes.

16. A method of controlling delivery of deep brain stimulation to a patient, the method comprising:
receiving, via a clinician programmer device, a first input from a user of the clinician programmer device, wherein the first input includes at least identification of a therapeutic window for one or more deep brain stimulation (DBS) parameters associated with testing of an electrode configuration of electrodes of an implantable stimulation lead that is coupled to an implantable pulse generator after implantation within a patient, and wherein the therapeutic window is defined by one or more DBS parameters used for test stimulation for a DBS benefit and a DBS side effect experienced by the patient during testing of the electrode configuration;
controlling, via wireless communications from the clinician programmer device to the implantable pulse generator, delivery of deep brain stimulation to the patient by the implantable pulse generator, wherein controlling delivery of deep brain stimulation to the patient includes modifying a DBS pulse amplitude for the electrode configuration under test; and
responsive to receiving a second input from the user of the clinician programmer device that identifies a side effect experienced by the patient for the electrode configuration under test, controlling delivery of deep brain stimulation to the patient by the implantable pulse generator by automatically decreasing the DBS pulse amplitude associated with the electrode configuration under test.

17. The method of claim 16, wherein automatically decreasing the DBS pulse amplitude includes automatically decreasing the DBS pulse amplitude without substantially interrupting deep brain stimulation of the patient according to the electrode configuration under test.

18. The method of claim 16, further comprising:
comparing the therapeutic window for the electrode configuration under test to a target value; and
alerting the user of the clinician programmer device that the target value has been reached.

19. The method of claim 18, further comprising:
receiving input from the user of the clinician programmer device whether to skip additional electrode screening after the target value has been reached.

20. The method of claim 16, further comprising:
comparing, by the clinician programmer device, power requirements associated with therapy thresholds for the electrode configuration under test; and
informing the user of the clinician programmer device whether the electrode configuration under test is likely to provide an optimal DBS program for the patient.

* * * * *

UNITED STATES PATENT AND TRADEMARK OFFICE
CERTIFICATE OF CORRECTION

PATENT NO. : 12,011,585 B2
APPLICATION NO. : 18/127448
DATED : June 18, 2024
INVENTOR(S) : Binith J. Cheeran et al.

It is certified that error appears in the above-identified patent and that said Letters Patent is hereby corrected as shown below:

In the Claims

At Column 20, Claim number 1, Line number 27, delete "DB S parameters" and replace with --DBS parameters--.

Signed and Sealed this
Thirteenth Day of August, 2024

Katherine Kelly Vidal
*Director of the United States Patent and Trademark Office*